United States Patent [19]
Killion

[11] Patent Number: 5,577,511
[45] Date of Patent: Nov. 26, 1996

[54] OCCLUSION METER AND ASSOCIATED METHOD FOR MEASURING THE OCCLUSION OF AN OCCLUDING OBJECT IN THE EAR CANAL OF A SUBJECT

[75] Inventor: Mead C. Killion, Elk Grove Village, Ill.

[73] Assignee: Etymotic Research, Inc., Elk Grove Village, Ill.

[21] Appl. No.: 412,334

[22] Filed: Mar. 29, 1995

[51] Int. Cl.$^6$ ..................................................... A61B 5/12
[52] U.S. Cl. .............................................. 128/746; 381/60
[58] Field of Search .............................. 128/746; 73/585; 381/60, 68, 68.6

[56] References Cited

U.S. PATENT DOCUMENTS

| | | | |
|---|---|---|---|
| 4,498,332 | 2/1985 | Bruckhoff | 128/746 |
| 4,809,708 | 3/1989 | Geisler et al. | 128/746 |
| 5,044,373 | 9/1991 | Northeved et al. | 128/746 |
| 5,317,273 | 5/1994 | Hanson et al. | 381/58 |

Primary Examiner—Angela D. Sykes
Assistant Examiner—Eric F. Winakur
Attorney, Agent, or Firm—McAndrews, Held & Malloy, Ltd.

[57] ABSTRACT

An instrument for measuring the degree of occlusion of an occluding object, such as an earmold, in the ear canal of a subject is set forth that overcomes the problems associated with prior art devices. The instrument includes a first microphone for transducing sound waves exterior to the ear canal into electrical signals and a first microphone for transducing sound waves within the ear canal into electrical signals. These electrical signals are respectively supplied to first and second logarithmic amplifiers. The first logarithmic amplifier is connected to receive the electrical signals from the first microphone and has a DC output signal that is logarithmically related to the peak amplitude value of the electrical signals received from the first microphone. The second logarithmic amplifier is connected to receive the electrical signals from the second microphone and has a DC output signal that is logarithmically related to the peak amplitude value of the electrical signals received from the second microphone. The DC output signals are supplied to a DC meter. The DC meter may be analog, digital, or may be a video display that provides a visual indication of the difference between the DC outputs of the first and second logarithmic amplifiers. A method of measuring the degree of occlusion of an occluding object in an ear canal is also set forth.

30 Claims, 5 Drawing Sheets

OCCLUSION METER AND ASSOCIATED METHOD FOR MEASURING THE OCCLUSION OF AN OCCLUDING OBJECT IN THE EAR CANAL OF A SUBJECT

TECHNICAL FIELD

The present invention relates to an apparatus for use in making ear measurements. More particularly, the present invention relates to an instrument and method for measuring the degree of occlusion of an occluding object in the ear canal.

BACKGROUND

In the fitting of a hearing aid, it is important to measure the occlusion of the actual earmold to determine the amount of leakage and whether there are any occlusion effects associated with the earmold. Measurement of the occlusion effect is performed by comparing sound pressure levels generated by the wearer's voice, for example, within the ear canal without the earmold with the sound pressure levels generated within the ear canal with the earmold in place. These sound pressure differences provide an indication of the degree of occlusion provided by the earmold. Similarly, measurement of earmold leakage can be made inside the ear canal (behind the earmold) with the sound level generated near the ear by an external sound source. The term "degree of occlusion" shall hereinafter be used to refer to the degree to which an occluding object, such as an earmold, prevents leakage and/or inhibits occlusion effects. In most instances, the measured difference between the sound pressure levels described above provide a quantitative measure of the degree of occlusion of an occluding object.

The failure of an earmold to properly seal and fit within the ear canal of a subject can result in unwanted repercussions. Without a close fit between the earmold and the ear canal wall, excessive leakage may result. This excessive leakage may result in annoying feedback that renders the hearing aid useless. With respect to occlusion effects, the bone conduction of the wearer's voice may be amplified when the ear is occluded. The hearing aid wearer's own voice is thus heard as being loud and distorted. This effect was noted by J. Zwislocki in his article entitled "Acoustic Attenuation Between The Ears", J. Acous. Soc. Amer. 25:752–759 (1953). The value of deeply sealed earmolds to eliminate this effect is discussed in an article by Mead Killion entitled "The 'Hollow Voice' Occlusion Effect" Hearing Aid Fitting—Theoretical and Practical Views, CH. III, pp. 231–242 (1988). It is therefore important in some fittings to ensure that the earmold seal extends far enough into the ear canal to eliminate this occlusion effect.

Testing of the quality of the earmold has heretofore been performed using expensive and bulky equipment such as a Frye 6500 available from Frye Electronics. Measurements with the Frye 6500 are performed sequentially. First, the subject being tested is provided with a sound stimulus without the earmold inserted. The sound stimulus is external when measuring leakage and self generated by the subject's own voice when measuring occlusion effects. The sound pressure level of the sound stimulus is measured by the Frye 6500 using a microphone probe that is positioned in the ear canal. The measured signals are stored and displayed as a frequency domain graph on a video display. After the reference measurements are made, the subject is provided with a further sound stimulus with the earmold inserted. The Frye 6500 again measures the sound pressure level within the ear canal as detected by the microphone probe. The frequency domain response of the sound detected in the ear canal with the earmold in place is then displayed on the video screen. Both frequency domain graphs are provided on the video display simultaneously to provide a visual comparison of the difference in sound pressure levels within the ear canal.

The Frye 6500 is a useful but complicated device which is often beyond the financial means of many audiologists. Additionally, it is a complex device that is often difficult to use without proper training. As such, audiologists must expend a substantial amount of otherwise valuable time to ensure that they are properly trained in use of the device. Further, the device is large and is not easily transported between examining rooms in the audiologist's offices.

SUMMARY OF THE INVENTION

An instrument for measuring the degree of occlusion of an occluding object, such as an earmold, in the ear canal of a subject is set forth that overcomes the problems associated with prior art devices. The instrument includes a first microphone for transducing sound waves exterior to the ear canal into electrical signals and a second microphone for transducing sound waves within the ear canal into electrical signals. These electrical signals are respectively supplied to first and second logarithmic amplifiers. The first logarithmic amplifier is connected to receive the electrical signals from the first microphone and. has a DC output signal that is logarithmically related to the amplitude value of the electrical signals received from the first microphone. The second logarithmic amplifier is connected to receive the electrical signals from the second microphone and has a DC output signal that is logarithmically related to the amplitude value of the electrical signals received from the second microphone. The DC output signals are supplied to a DC meter. The DC meter may be analog, digital, or may be a video display that provides a visual indication of the difference between the DC outputs of the first and second logarithmic amplifiers.

In accordance with one embodiment of the invention, the logarithmic amplifiers and DC meter are provided in a single hand-held housing unit. This allows audiologists to easily transport the instrument between patients at different locations.

In a further embodiment of the invention, the accuracy of the occlusion measurements is further enhanced by filtering each electrical signal supplied from each microphone to the respective logarithmic amplifier. More particularly, the filters provide low frequency components of the electrical signals to the respective logarithmic amplifiers.

A method for measuring the degree of occlusion of an occluding object disposed in the ear canal of a subject is also set forth. In accordance with the method, an occluding object is inserted into the ear canal. A sound stimulus is then provided. The sound pressure levels generated by the sound stimulus are simultaneously measured at a point exterior to the ear canal and at a point interior to the ear canal. These measured sound pressure levels are compared to one another to provide an indication of the degree of occlusion.

In accordance with one embodiment of the method, the sound pressure levels are simultaneously measured by measuring the sound pressure levels exterior to the ear canal and interior to the ear canal using first and second microphones, respectively. The first microphone measures sound pressure levels exterior to the ear canal and transduces sound it receives into electrical signals. The second microphone concurrently measures the sound pressure level within the ear canal and transduces sounds it receives through a microphone probe tube disposed in the ear canal into electrical signals. These electrical signals are converted into a first DC signal that is logarithmically related to the electrical signals received from the first microphone and a second DC signal that is logarithmically related to the electrical signals received from the second microphone. The difference between the first and second DC signals provides the indication of the degree of occlusion. This difference may be visually displayed on a meter.

DETAILED DESCRIPTION OF THE PREFERRED EMBODIMENT

Figure 1:
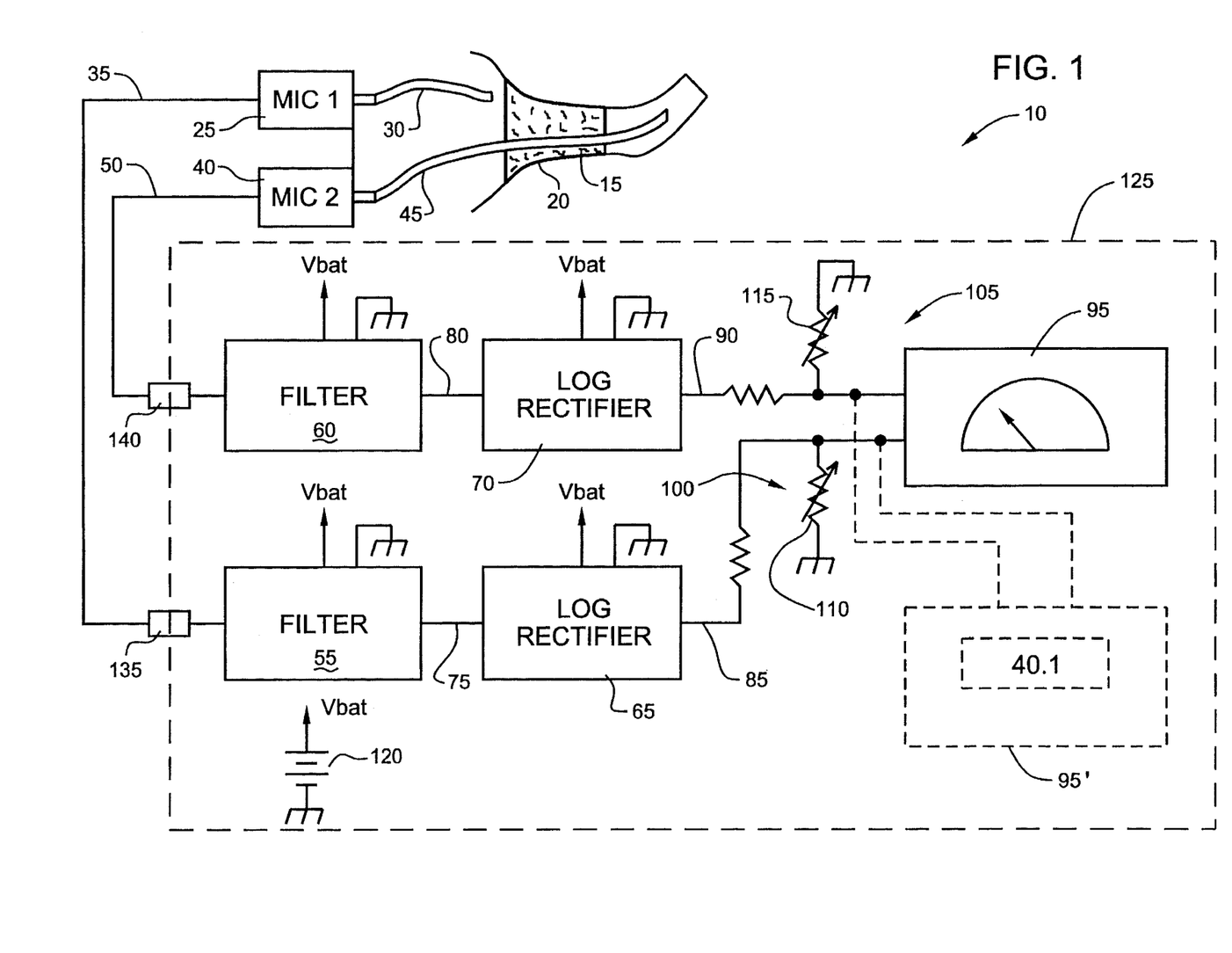
FIG. 1 is a schematic block diagram of one embodiment of an occlusion meter in accordance with the present invention

An instrument 10 for measuring the degree of occlusion of an occluding object 15 in the ear canal 20 of a subject is shown in FIG. 1. As illustrated, the instrument 10 includes a first microphone 25 that is connected to receive sound waves through an inlet or probe tube 30 that extends to a position proximate the exterior of the ear canal 20. Microphone 25 functions as a reference microphone and measures sound pressure levels exterior to the ear canal 20, transducing sound waves to electrical signals that are supplied along one or more lines 35. The instrument 10 further includes a second microphone 40 that is connected to receive sound waves through probe tube 45 probe tube 45 extends into the ear canal 20 to a position within the ear canal that allows sound pressure levels within the ear canal to be detected by the second microphone 40. The probe tube may be constructed in accordance with the teachings of U.S. Ser. No. 08/407,317 filed Mar. 20, 1995, entitled "Microphone probe Tubing." The second microphone 40 transduces sound waves from the ear canal into electrical signals that are supplied along one or more lines 50.

The electrical signals supplied along lines 35 and 50 are optionally applied to respective filters 55 and 60. The filters 55 and 60 are preferably designed to pass low frequency components of the electrical signals and, for example, may be either low pass filters or bandpass filters that are designed to pass frequency components around 250 Hz. Use of the filters 55 and 60 takes advantage of the fact that a non-occluded ear generally has the same sound pressure levels exterior to the ear canal and interior to the ear canal for low frequency signal components; at that frequency, the SPL proximate the occluded ear may thus be used as a good representation of the SPL in the unoccluded ear. This permits the elimination of the first step in the normal two-step process described above in connection with the Frye 6500, thus making for a more rapid and accurate measurement.

Accuracy is increased because a single source level is used, and the measured difference is generally independent of sound pressure level. The filters 55 and 60 thus facilitate a more accurate measure of the degree of occlusion afforded by the occluding object 15, such as an earmold.

The instrument 10 also includes a first logarithmic rectifier 65 and a second logarithmic rectifier 70. The first logarithmic rectifier 65 receives electrical signals from the first microphone 25 along line(s) 35, or from the filter 55 along one or more lines 75. Similarly, the second logarithmic rectifier 70 receives electrical signals from the second microphone 25 along line(s) 50, or from the filter 60 along one or more lines 80. The logarithmic rectifiers 65 and 70 convert the electrical signals at lines 75 and 80, respectively, into a DC signal having an amplitude that is logarithmically related to the amplitude of the signals at lines 75 and 80. The DC signal generated in response to the signal at line 75 is available on output line 85 while the DC signal generated in response to the signal at line 80 is available on output line 90. The signals on output lines 85 and 90 are supplied to a meter 95 that, for example, may be a voltmeter that measures the difference between the voltage of the signal on line 85 and the voltage of the signal on line 90. The meter may be calibrated in decibels and may provide an analog display, such as shown at meter 95, or a digital display, such as shown at meter 95' (shown here in phantom outline). Other display formats may also be used.

Optionally, a voltage divider circuit may be interposed between one or both of the logarithmic rectifiers 65 and 70 and their respective meter terminals. Two voltage dividers are illustrated at 100 and 105 in FIG. 1. Each of the voltage dividers 100 and 105 include a respective variable resistor 110, 115, such as a trim pot, that allows adjustment of the output voltage from the respective rectifier 65, 70 to the meter 95. This facilitates zeroing of the meter 95 to obtain a more accurate occlusion measurement.

The filters 55, 60, the logarithmic rectifiers 85, 90, and the meter 95 may receive power from a battery 120 and be enclosed in a single housing 125. The housing 125 may be hand held since the components 55, 60, 85, 90, and 95 may be constructed to be compact and lightweight. The signals along lines 35 and 50 from microphones 25 and 40 may be connected to the components within the housing 125 by, for example, input jacks 135 and 140 or may be hard-wired with the circuit components.

Figure 2:
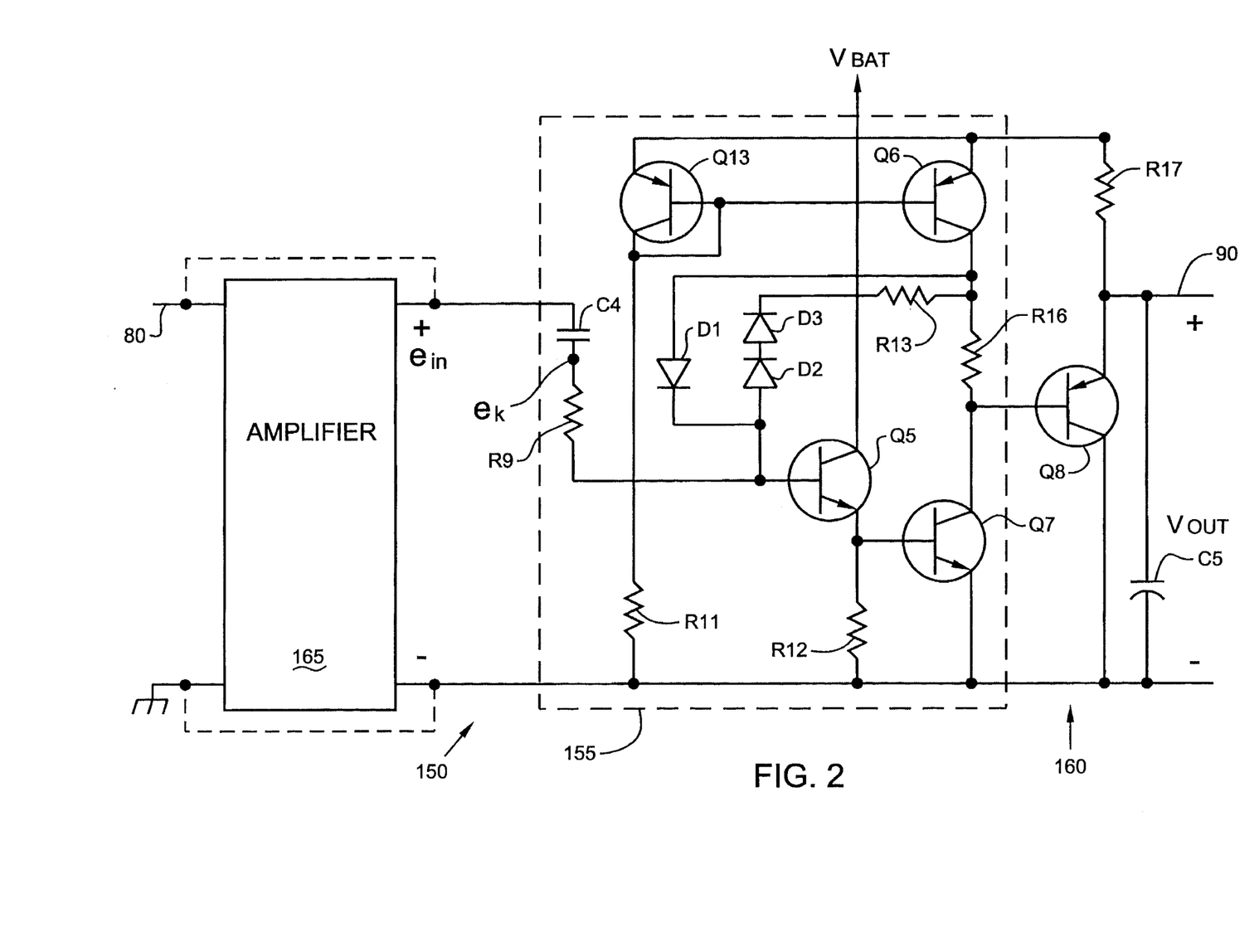
FIG. 2 is a schematic diagram of a logarithmic amplifier suitable for use in the embodiment of FIG. 1.

FIG. 2 illustrates one embodiment of a logarithmic rectifier circuit 150 that may be utilized for the logarithmic rectifiers 65 and 70 of FIG. 1. The logarithmic rectifier circuit 150 includes a logarithmic AC amplifier 155 and a peak detector 160. In the case of logarithmic rectifier 70, the logarithmic AC amplifier 155 receives signals either directly from line 80 or through a linear amplifier 165. The logarithmic AC amplifier 155 has a very high input impedance and roughly 60 dB of open loop gain. The diode D1 connected in parallel with diodes D2 and D3 and resistor R13 function as a nonlinear feedback impedance which in cooperation with the input resistor R9 provides a closed loop gain which is related to the input signal voltage $e_{in}$ in such a way that the peak voltage at the collector of Q7 is proportional to the logarithm of the peak AC voltage $e_k$ developed at the junction of the capacitor C4 and resistor R9. The voltage at the collector of Q7 will have a DC resting value of roughly 850 mV DC with an AC input of 0.3 mV or less and a negative going AC peak value which increases logarithmically at a rate of approximately 220 mV for each factor of ten increase in input signal voltage $e_k$.

With low values of resistor R13, this nearly exact logarithmic relationship exists over a 60 dB range of AC input voltages $e_k$ extending from a 0.3 mV to 300 mV. With higher values of resistor R3, a deviation toward linear operation is obtained at higher input levels.

The sum of the base emitter offset voltages of Q5 and Q7 produces a relatively high DC input voltage so that two series diodes (D2 and D3) rather than one may be used in the feedback loop without incurring the undesirable negative voltage clipping which would otherwise occur due to saturation of transistor Q7. A wide range of operation combined with a high (220 mV/decade) sensitivity of the logarithmic amplifier 155 is thus made possible for operation with, for example, a 1.3 to 1.6 volt supply.

Transistor Q8, resistor R17, and capacitor C5 provide a peak detection rectifier 160. Transistor Q8 is used in order to provide a high input impedance so the rectifier 160 does not load down the output of the logarithmic AC amplifier 155. Resistor R17 and capacitor C5 determine the attack and release time of the circuit which, for example, may be an attack time of 3 milliseconds and a release time of about 50 milliseconds. The rectified DC output signal is supplied along line 90 in the case of logarithmic rectifier 70 of FIG. 1.

Figure 3A:
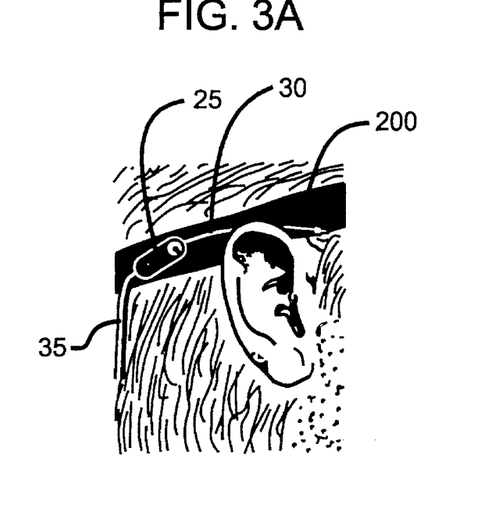
FIGS. 3A–3D illustrate how the microphones may be mounted to the subject.
Figure 3B:
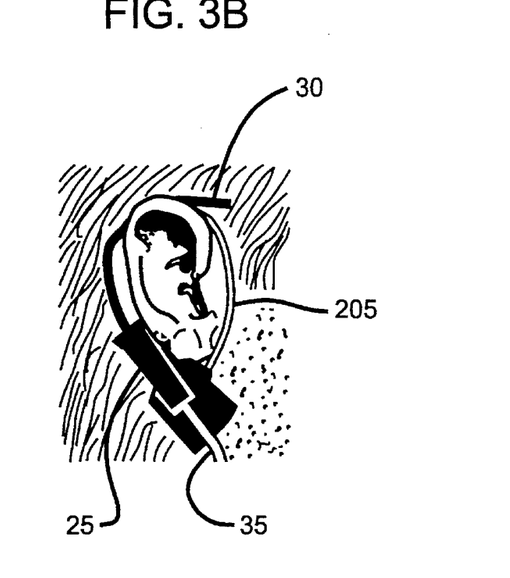
Figure 3C:
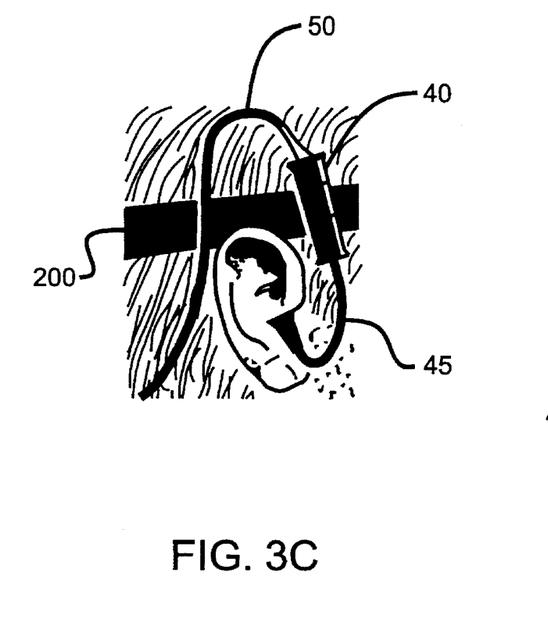
Figure 3D:
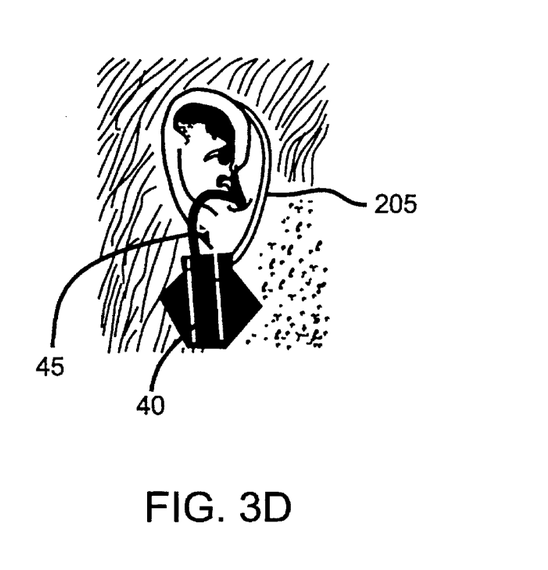

FIGS. 3A–3D illustrate exemplary securement of the microphones 25 and 40 and their respective probe tubes 30 and 45 to the subject under test. In FIG. 3A, the first microphone 25 is secured with a Velcro™ securement to a headband 200 that is worn by the subject. In FIG. 3B, the microphone 25 is secured by, for example, a Velcro™ securement to an ear hook 205. FIGS. 3C and 3D illustrate similar securements for the microphone 40 and tube 45. Although not explicitly illustrated in the foregoing figures, it will be recognized that a single headband 200 may secure both microphones 25 and 40 and their respective tubes 30 and 45 to the subject. Alternate arrangements combining these securement types are likewise suitable.

Figure 4:
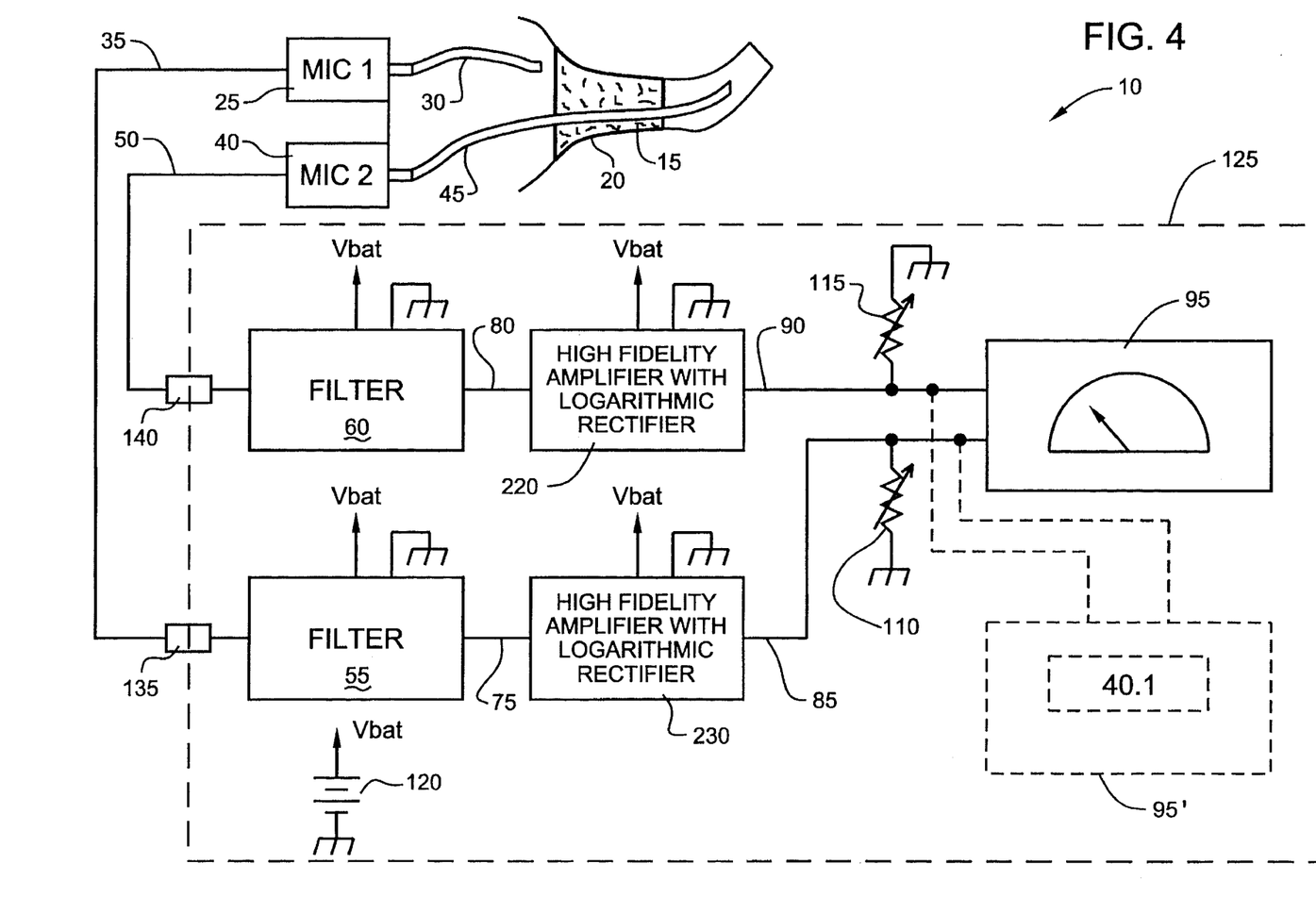
FIG. 4 is a schematic block diagram of a further embodiment of an occlusion meter constructed in accordance with the present invention.

FIG. 4 illustrates an alternative embodiment of the instrument 10. The illustrated embodiment is similar in most respects to the embodiment illustrated in FIG. 1. Unlike the embodiment illustrated in FIG. 1, however, the logarithmic rectifiers 65 and 70 have been replaced with high fidelity amplifiers 220 and 230 that include respective logarithmic rectifiers that have rectified logarithmic DC signals available at one or more of the circuit output lines. One type of high fidelity amplifier suitable for use in the illustrated embodiment is the K-AMP™ hearing aid amplifier that is commercially available from ETYMOTIC RESEARCH™ Inc. of Elk Grove, Ill. The principal components of the K-AMP™ are illustrated and described in U.S. Pat. No. 5,131,046, issued Jul. 14, 1992, to Killion et al, which is hereby incorporated by reference in its entirety.

Figure 5:
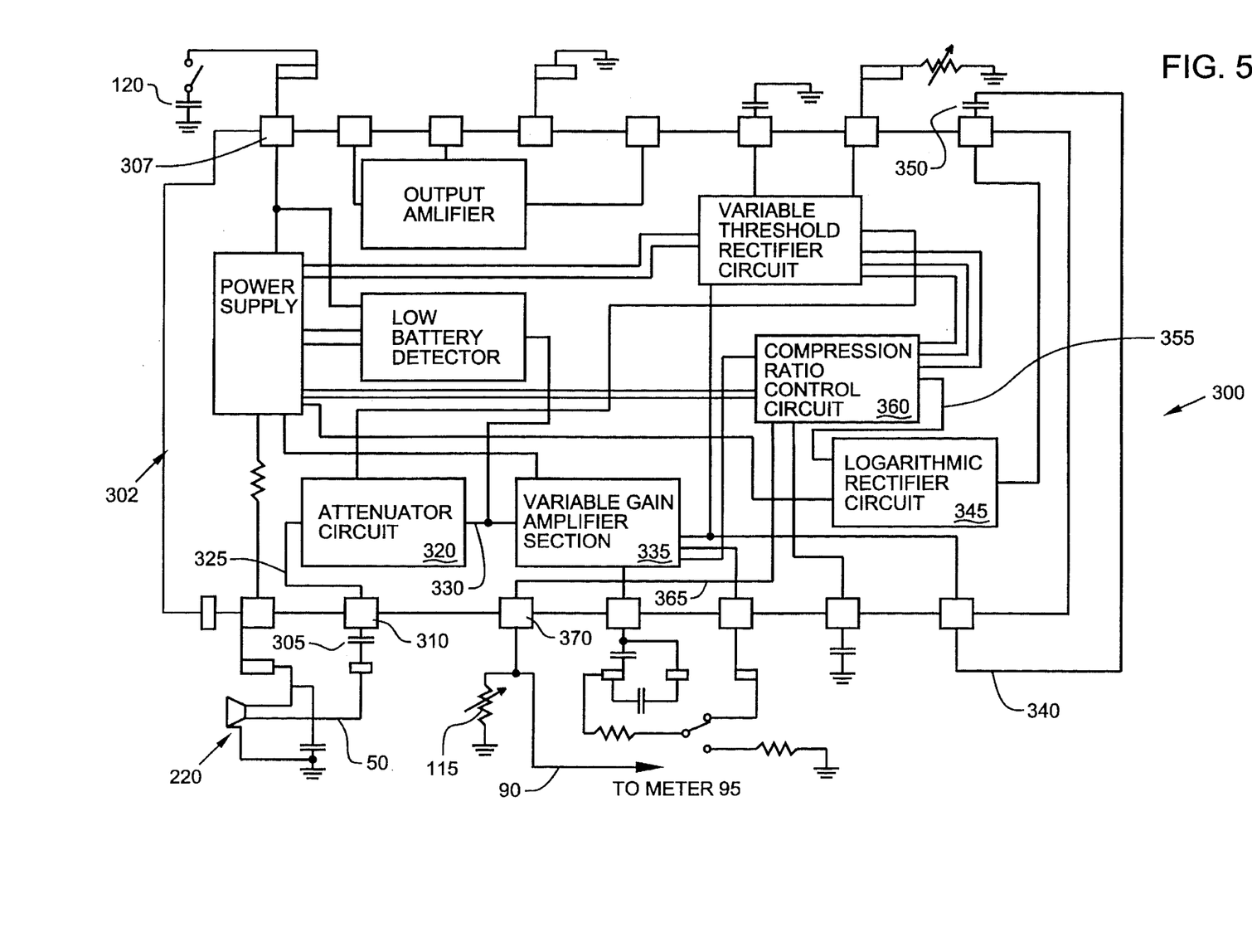
FIG. 5 is a schematic diagram of a high fidelity amplifier having a logarithmic rectifier for use in the embodiment of FIG. 4.

FIG. 5 is a block diagram of the high fidelity amplifier disclosed in the '046 patent. In FIG. 5, reference numeral 300 generally designates a high fidelity amplifier, such as the high fidelity amplifier 220 of FIG. 4. In the illustrated embodiment, the circuitry includes components on an integrated circuit chip which is generally designated by reference numeral 302 and circuit components which are external to the chip 302 that are adjustable or of selectable size and/or too large or otherwise such that it is not possible or desirable to include them on the chip 302. Power is supplied to the integrated circuit 302 from battery 120 at terminal pad 307. It will be recognized that the amplifier 300 may function as a hearing aid amplifier.

The high fidelity amplifier 300 is connected, for example, to the output line 80 of filter 60, or, as illustrated in FIG. 5, to receive electrical signals directly from the second microphone 40 through a capacitor 305 at chip terminal 310. The electrical signals from the microphone are supplied to the input of an attenuator circuit 320 along line 325. The output of the attenuator circuit 320 is supplied along line 330 to the input of a variable gain amplifier section 335. Variable gain amplifier 335 provides an electrical output signal along line 340 to the input of a logarithmic rectifier circuit 345 through external capacitor 350. The signal along line 340 is an amplified version of the signal at line 50 that is received from the microphone 220.

The logarithmic rectifier circuit 345 provides a pulsed AC output signal at line 355 to the input of a compression ratio control circuit 360. The voltage amplitude of the pulsed AC output signal is logarithmically related to the sound pressure level detected at microphone 220. The AC signal output is rectified by components internal to the compression ratio control circuit 360 (see FIG. 5 of '046 patent) to provide a DC signal that is logarithmically related to the sound pressure level at microphone 50. More specifically, it is related to the AC signal at line 355 from the logarithmic rectifier circuit 345. This rectified signal is supplied along line 365 and is available at chip terminal pad 370 where it is supplied, in the case of amplifier 220 of FIG. 4, to meter 95 along line 90. A variable resistor 115 is provided between terminal 370 and ground to adjust the sensitivity of the attenuator circuit 320 and variable gain amplifier 335.

The foregoing description of the high fidelity amplifier circuit 300 has omitted many of the unnecessary details of operation of the circuit for the sake of simplicity. A detailed description of the specific circuit components that may be used to implement each of the circuits illustrated in FIG. 5 can be found in the foregoing '046 patent, it being recognized, however, that such circuitry is merely exemplary.

Other circuits for providing electrical signals that are logarithmically related to the sound pressure levels at microphones 25 and 40 may also be utilized in place of logarithmic rectifiers 65 and 70, the embodiments described herein being merely exemplary and not limiting. For example, a digital signal processor chip (DSP) with a built-in linear or logarithmic A/D converter may be used. If a linear A/D is used, the DSP may calculate the logarithm of the digitized signal before display.

The instruments 10 described herein may be used to check the degree of occlusion of an earmold. When testing for leakage, an external sound signal is generated by the audiologist. If filters 55 and 60 are not utilized in the instrument 10, the sound signal preferably is a low frequency sound signal or tone. Even more preferably, the sound signal will be a tone having a frequency of about 250 Hz. If filters are used, the sound stimulus may be the audiologist's own voice reciting, for example, the vowel sound "EEE". The meter 95 displays the difference between the sound pressure level exterior to the ear canal 20, as detected by microphone 25, and the sound pressure level within the ear canal 20, as detected by microphone 40. The difference between the signals indicates how well the earmold is sealed within the ear canal 20. The greater the difference that is detected, the better the seal.

When testing for occlusion effects, the subject under test produces a sound with his voice, for example, by reciting the vowel sound "EEE". The meter 95 displays the difference between the sound pressure level exterior to the ear canal 20 as detected by microphone 25 and the sound pressure level within the ear canal 20 as detected by microphone 40. The difference between the signals indicates how well the earmold prevents the occlusion effect. If the sound pressure level within the ear canal is greater than the sound pressure level that is detected exterior to the ear canal, the earmold may need to be vented and/or sealed more deeply within the ear canal.

Although the present invention has been described with reference to a specific embodiment, those of skill in the art will recognize that changes may be made thereto without departing from the scope and spirit of the invention as set forth in the appended claims.

I claim as my invention:

1. An instrument for use in obtaining measurements of an ear having an ear canal, the instrument comprising:
   a) a first microphone for transducing sound waves exterior to the ear canal into electrical signals;
   b) a second microphone for transducing sound waves in the ear canal into electrical signals;
   c) a first logarithmic amplifier having a DC output signal that is logarithmically related to electrical signals received at an input thereof;
   d) a first low pass filter having an input connected to receive the electrical signals from the first microphone and an output connected to the input of the first logarithmic amplifier;
   e) a second logarithmic amplifier having a DC output signal that is logarithmically related to electrical signals received at an input thereof;
   f) a second low pass filter having an input connected to receive the electrical signals from the second microphone and an output connected to the input of the second logarithmic amplifier; and
   g) a DC meter connected to receive the DC output signals from the first and second logarithmic amplifiers.

2. An instrument as claimed in claim 1 and further comprising a housing, the first and second logarithmic amplifiers and the DC meter being disposed in the housing.

3. An instrument as claimed in claim 2 wherein the housing is dimensioned so that it may be hand held.

4. An instrument as claimed in claim 2 wherein the DC meter is calibrated in decibels.

5. An instrument as claimed in claim 1 and further comprising mounting means for mounting the first microphone at a position proximate the ear.

6. An instrument as claimed in claim 1 and further comprising:
   d) an occluding object adapted to be disposed in the ear canal; and
   e) a probe tube for conducting sound from the ear canal to a sound port input of the second microphone, the probe tube extending from the ear canal and around the occluding object to the sound port input.

7. An instrument as claimed in claim 1 and further comprising mounting means for mounting the second microphone at a position proximate the ear.

8. An instrument as claimed in claim 1 wherein the first and second low pass filters have a cutoff frequency above 250 Hz.

9. An instrument as claimed in claim 1 wherein the first and second low pass filters are bandpass filters having a low center frequency.

10. An instrument as claimed in claim 1 wherein the first and second low pass filters are bandpass filters having a center frequency of approximately 250 Hz.

11. An instrument as claimed in claim 1 and further comprising means for zeroing the meter.

12. An instrument as claimed in claim 11 wherein the means for zeroing the meter comprises a voltage divider circuit having an adjustable resistor, the voltage divider circuit being connected to divide the DC output signal from either the first or second logarithmic amplifier to the meter.

13. An instrument as claimed in claim 11 wherein the means for zeroing the meter comprises:
   a) a first voltage divider circuit having an adjustable resistor, the voltage divider circuit being connected to divide the DC output signal from the first logarithmic amplifier to the meter; and
   b) a second voltage divider circuit having an adjustable resistor, the voltage divider circuit being connected to divide the DC output signal from the second logarithmic amplifier to the meter.

14. An instrument for use in obtaining measurements of an ear having an ear canal, the instrument comprising:
   a) a first microphone for transducing sound waves exterior to the ear into electrical signals;
   b) a second microphone for transducing sound waves in the ear canal into electrical signals;
   c) a first frequency dependent filter having an input connected to receive the electrical signals from the first microphone and further having an electrical signal output, the first frequency dependent filter having a response that passes low frequencies and filters high frequencies;
   d) a second frequency dependent filter having an input connected to receive the electrical signals from the second microphone and further having an electrical signal output, the second frequency dependent filter having a response that passes low frequencies and filters high frequencies;
   e) a first logarithmic amplifier connected to receive the electrical signals from the electrical signal output of the first frequency dependent filter, the first logarithmic amplifier having a DC output signal that is logarithmically related to the electrical signals received from the first frequency dependent filter;
   f) a second logarithmic amplifier connected to receive the electrical signals from the electrical signal output of the second frequency dependent filter, the second logarithmic amplifier having a DC output signal that is logarithmically related to the electrical signals received from the second frequency dependent filter;
   g) a DC meter connected to receive the DC output signals from the first and second logarithmic amplifiers; and
   h) a hand-held housing for containing the DC meter, the first and second frequency dependent filters, and the first and second logarithmic amplifiers.

15. An instrument as claimed in claim 14 wherein the DC meter is calibrated in decibels.

16. An instrument as claimed in claim 14 and further comprising mounting means for mounting the first microphone at a position proximate the ear.

17. An instrument as claimed in claim 14 and further comprising:
   i) an occluding object adapted to be disposed in the ear canal; and
   j) a probe tube for conducting sound from the ear canal to a sound port input of the second microphone, the probe tube extending from the ear canal an around the occluding object to the sound port input.

18. An instrument as claimed in claim 17 and further comprising mounting means for mounting the second microphone at a position proximate the ear.

19. An instrument as claimed in claim 14 wherein the first and second frequency dependent filters are low pass filters having a cutoff frequency above 250 Hz.

20. An instrument as claimed in claim 14 wherein the first and second frequency dependent filters are bandpass filters having a low center frequency.

21. An instrument as claimed in claim 20 wherein the first and second frequency dependent filters are bandpass filters having a center frequency of approximately 250 Hz.

22. An instrument as claimed in claim 14 and further comprising means for zeroing the DC meter.

23. An instrument as claimed in claim 22 wherein the means for zeroing the meter comprises a voltage divider circuit having an adjustable resistor, the voltage divider circuit being connected to divide the DC output signal from either the first or second logarithmic amplifier to the meter.

24. An instrument as claimed in claim 22 wherein the means for zeroing the meter comprises:
  a) a first voltage divider circuit having an adjustable resistor, the voltage divider circuit being connected to divide the DC output signal from the first logarithmic amplifier to the meter; and
  b) a second voltage divider circuit having an adjustable resistor, the voltage divider circuit being connected to divide the DC output signal from the second logarithmic amplifier to the meter.

25. A method for measuring the degree of occlusion of an occluding object disposed in an ear canal of a subject, the method comprising the steps of:
  a) inserting the occluding object into the ear canal;
  b) providing a sound stimulus;
  c) simultaneously measuring sound pressure levels of the low frequency components of the sound stimulus at positions exterior to the ear canal and within the ear canal to the exclusion of high frequency components; and
  d) simultaneously comparing the measured sound pressure levels to provide an indication of the degree of occlusion.

26. A method as claimed in claim 25 wherein the step of simultaneously measuring sound pressure level comprises the steps of:
  a) measuring the sound pressure level exterior to the ear canal with a first microphone, the first microphone transducing sound received by the first microphone into electrical signals;
  b) concurrently measuring the sound pressure level within the ear canal using a second microphone connected to receive sound through a microphone tube, the microphone tube connected to the second microphone and extending into the ear canal, the second microphone transducing sound received by the second microphone into electrical signals; and
  c) low pass filtering the signals received from the first and second microphones.

27. A method as claimed in claim 26 wherein the step of simultaneously comparing the measured sound pressure levels comprises the steps of:
  a) converting the filtered electrical signals from the first microphone into a first DC signal that is logarithmically related to the electrical signals received from the first microphone;
  b) converting the filtered electrical signals from the second microphone into a second DC signal that is logarithmically related to the electrical signals received from the second microphone, the first and second DC signals differing from one another to provide the indication of the degree of the occlusion effect.

28. A method as claimed in claim 26 wherein the step of simultaneously comparing the measured sound pressure levels comprises the steps of:
  a) coverting the filtered electrical signals from the first microphone into a first DC signal that is logarithmically related to the filtered electrical signals received from the first microphone; and
  b) converting the filtered electrical signals from the second microphone into a second DC signal that is logarithmically related to the filtered electrical signals received from the second microphone, the first and second DC signals differing from one another to provide the indication of the degree of occlusion.

29. A method as claimed in claim 28 and further comprising the step of measuring the difference between the first and second DC signals and using the measured difference to provide a visual display of the measured degree of occlusion.

30. A method for measuring the degree of occlusion of an occluding object disposed in an ear canal of a subiect, the method comprising the steps of:
  a) inserting the occluding object into the ear canal;.
  b) providing a low frequency sound stimulus having a frequency spectrum that is principally about or below 250 Hz;
  c) simultaneously measuring sound pressure levels of the sound stimulus at positions exterior to the ear canal and within the ear canal; and
  d) simultaneously comparing the measured sound pressure levels to provide an indication of the degree of occlusion.

* * * * *

UNITED STATES PATENT AND TRADEMARK OFFICE
CERTIFICATE OF CORRECTION

PATENT NO.   : 5,577,511
DATED        : November 26, 1996
INVENTOR(S)  : Killion It is certified that error appears in the above-identified patent and that said Letters Patent is hereby corrected as shown below:

Column 3, line 44, delete "45 probe" and insert --45. Probe--.

Column 3, line 49, delete "probe" and insert -- Probe -- therefore.

Claim 28, column 10, line 20, delete "coverting" and insert --converting -- therefore.

Signed and Sealed this

Eighth Day of April, 1997

*Attest:*

BRUCE LEHMAN

*Attesting Officer*     *Commissioner of Patents and Trademarks*